United States Patent [19]
Shields

[11] Patent Number: 5,858,004
[45] Date of Patent: Jan. 12, 1999

[54] HEAD PROJECTIONS ON SHIELDED BUTTERFLY NEEDLE ASSEMBLIES

[76] Inventor: Jack W. Shields, 1950 Las Tunas Rd., Santa Barbara, Calif. 93103

[21] Appl. No.: 699,039

[22] Filed: Aug. 19, 1996

[51] Int. Cl.6 .................................................. A61M 5/00
[52] U.S. Cl. ............................................................. 604/177
[58] Field of Search ..................... 604/177, 192, 604/198, 263, 162, 110

[56] References Cited

U.S. PATENT DOCUMENTS

| | | | |
|---|---|---|---|
| 4,585,444 | 4/1986 | Harris | 604/177 |
| 4,676,783 | 6/1987 | Jagger et al. | 604/177 X |
| 5,266,072 | 11/1993 | Utterberg | 604/177 |
| 5,562,636 | 10/1996 | Utterberg | 604/177 X |
| 5,562,637 | 10/1996 | Utterberg | 604/177 X |

*Primary Examiner*—John D. Yasko

[57] ABSTRACT

I describe a dorsal head-like projection for stabilizing the leading end of a shielded winged intravenous (IV) infusion assembly such that venous bleeding and anchoring of the assembly are simultaneously controlled with a finger tip on the projection, while the free hand retracts the infusion needle via trailing tubing into the body or into a sliding shield without exposure of the needle during or after use for giving an infusion or withdrawing blood.

6 Claims, 1 Drawing Sheet

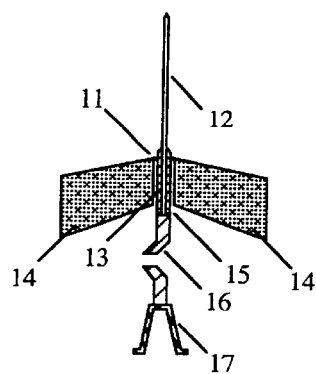
FIG. 1 (Prior Art)
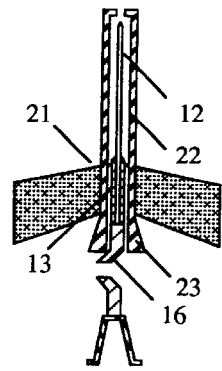
FIG. 2 (Prior Art)
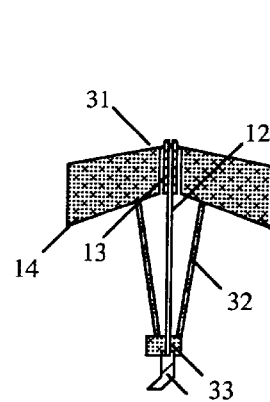
FIG. 3 (Prior Art)
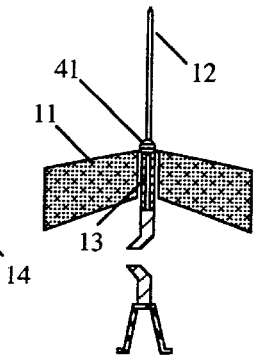
FIG. 4 (Projected Art)
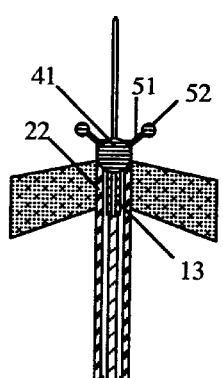
FIG. 5
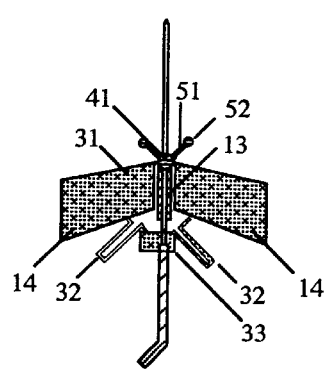
FIG. 6
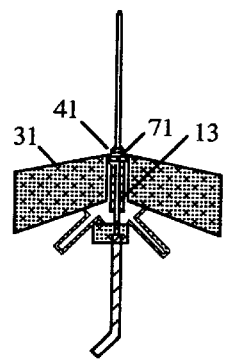
FIG. 7
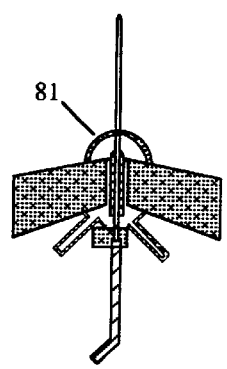
FIG. 8
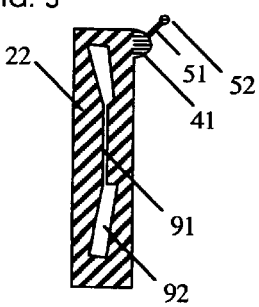
FIG. 9
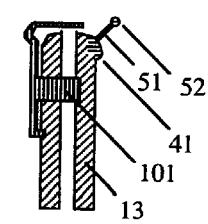
FIG. 10
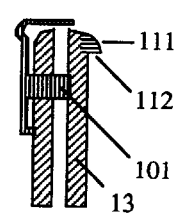
FIG. 11
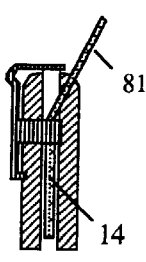
FIG. 12

HEAD PROJECTIONS ON SHIELDED BUTTERFLY NEEDLE ASSEMBLIES

FIELD OF THE INVENTION

This invention relates to the comfort of patients and the protection of health care workers (HCW) from blood borne pathogens during the use of "butterfly" or winged infusion assemblies for giving intravenous (IV) infusions or withdrawing venous blood.

PRIOR ART

Winged infusion assemblies with leading hollow-bore steel needles have proven very useful in medical practice and are well tolerated by patients. Owing to increasing risks of blood borne virus infections, including HIV, HBV, HCV, HTLV and Ebola, from accidental needle sticks during the use of such assemblies, safer embodiments currently include sliding traps into which the tip, bevel and shank of the needle are captured after use in a patient. Outstanding examples are currently sold in the form of VACUTAINER® Brand Safety-Lok™ Blood Collection Sets manufactured by Becton-Dickinson and in the ANGEL WING™ SAFETY NEEDLE SYSTEM manufactured by Sherwood Medical These embodiments without tethers customarily involve withdrawing the needle from a patient's vein before the needle is safely captured and specify no means for effective control of venous bleeding during withdrawal of the hollow needle.

Patent searches that reveal that Utterberg in U.S. Pat. No. 5,112,311 (May 12, 1992) claimed a sliding needle trap permanently attached to the body for entrapping the wings of a butterfly needle assembly by means of paired side slits and slots when the trailing tubing is retracted with one hand and an anchoring piece projecting forward from the leading end of the sliding trap is used by the other hand to tether the sliding trap such that the wings can be trapped into paired trailing slots. Fayngold in U.S. Pat. No. 5,120,320 (Jun. 9, 1992), assigned to Becton-Dickinson, omitted the anchoring tether, but claimed a trailing two piece shielding trap for butterfly needles wherein a flat top piece, when joined to a U-shaped bottom piece with slits and slots forms a permanently attached sliding winged infusion needle trap like that claimed by Utterberg in a version longitudinally hinged. Burns in U.S. Pat. No. 5,192,275 (Mar. 9, 1993), assigned to Becton-Dickinson, claimed the addition of a pull tab on the trailing end of a sliding trap essentially like that claimed by Fayngold and Utterberg, such that the user can grasp the pull tab by means of two fingers of one hand and use the remaining fingers, heel or wrist of one hand to pull the wings back into trailing slots by means of trailing tubing, after the needle has been withdrawn from the vein of a patient, as exemplified in the form of VACUTAINER® Brand Safety-Lok™ Blood Collection Sets. Pursuant to U.S. Pat. No. 5,176,655 by McCormick (January, 1993), Sherwood Medical Corporation now produces the ANGEL WING™ SAFETY NEEDLE SYSTEM which differs from the former in that paired trailing tethers extending from the trailing aspects of the butterfly needle wings are employed to limit the trailing excursion of a special hub holding a needle which slides within the body of a winged infusion assembly wherein the leading end is fitted with a spring clip for limiting forward excursion of sharp end of the needle after complete retraction into the assembly by means of one hand whose heel or wrist pulls back on the trailing tubing after the needle has been withdrawn from a patient's vein. In U.S. Pat. No. 5,350,368 (Sep. 27, 1994) Shields claimed tethered open-ended traps with slits and slots which slide forward over trailing tubing to trap the wings and, secondarily, safely entrap the needles during standard bi-manual operation of winged infusion assembles with large bore needles. The instant invention, formally conceived Aug. 16, 1995 and provisionally filed Aug. 20, 1995, shares features with all the former, but is distinctive in that a dorsal head projection for finger placement is embodied, but not projecting forward, on the leading end of a permanently attached sliding trap with trailing pairs of slits and slots, or on the leading end of the body in a winged infusion assembly having a trailing tethering mechanism for a sliding needle hub, such that the user can simultaneously control venous bleeding and stabilize the leading end of the assembly with one hand, while the other hand retracts the needle into the trap by means of trailing tubing without exposing the bevel or shaft of the needle. In essence, the instant invention is unique in claiming a dorsal head projection for finger control on the leading end of a winged infusion assembly having trailing means for safely capturing the beveled tip and shank of the infusion needle.

SUMMARY

I describe a projection for finger placement on the leading end of a shielded winged intravenous (IV) assembly such that venous bleeding and anchoring of the assembly are effectively controlled with a finger tip, while the other free hand retracts the leading hollow needle by means of trailing attached tubing into a sliding shield or into the "butterfly" body without exposure of the needle during or after use for giving an infusion or withdrawing blood. The advantages of the instant invention over comparable items are:

a. Efficient control of patients' venous bleeding or oozing during and after withdrawal of the hollow needle with minimal patient discomfort, and maximal user safety.

b. The tip, bevel and shank of the hollow needle are never exposed after IV insertion and, thus, minimize hazards to users, by-standers and clean-up personnel.

c. Manipulation is standard and customary, and almost precisely like that during use of a standard, unshielded winged infusion assembly.

d. Little additional cost for adding the head projection to winged infusion assemblies having means for safely shielding the infusion needle after intravenous use.

BRIEF DESCRIPTION OF DRAWINGS

FIG. 1: A schematic axial view of a prior art standard unshielded winged infusion assembly. (Scale 1:1 in FIGS. 1–8).

FIG. 2: A schematic axial view of the current art, as seen in VACUTAINER® Safety-Lok™ with the needle captured in a sliding trap.

FIG. 3: A schematic axial view of the current art, as seen in ANGEL WING™Safety Needle System with the needle captured inside the body.

FIG. 4: A schematic axial view of a standard unshielded winged infusion set with a butterfly-like head projection on the leading end of the body.

FIG. 5: A schematic axial view of FIG. 2 having a head and antennae on the leading end of a sleeve sliding over the body, and lacking a trailing projection for finger placement on the sleeve.

FIG. 6: A schematic axial view of FIG. 3, showing a head and antennae on the leading end of the butterfly body to optimize anchoring with a finger tip.

FIG. 7: A schematic axial view of FIG. 3, looking down on a dorsal head-like projection on the leading end of the "butterfly" body.

FIG. 8: A schematic axial view of FIG. 3, showing a leading loop-like tether projecting from the leading edge of the "butterfly" wings.

FIG. 9: A schematic axial view of a sleeve sliding over the butterfly body and rotated 90 degrees in a scale of ±2:1 in width. This figure shows a low profile head with projecting antennae.

FIGS. 10–12 are oriented and scaled similarly to show the different forms of head profiles, along with needle trapping means. Each corresponds to the view depicted directly above.

FIG. 10: Shows a ventral spring-clip on the left and a lower profile head with antennae angled dorsally.

FIG. 11: Shows a longitudinal flange-like head.

FIG. 12: Shows a looping tether emanating from the leading edge of the wings.

DESCRIPTION OF PREFERRED EMBODIMENTS

As shown in FIG. 1, a standard unshielded winged infusion assembly 11 comprises a leading hollow needle 12, a body 13 which holds the needle 12, paired wings 14 attached to the body 13, a hub 15 on the trailing end of the needle 12, trailing tubing 16 attached to the hub 15 and standard flanged connector 17 on the trailing end of the tubing which fits a luer-slip or Luer-Lok connector on a syringe or on separate tubing used to fill the butterfly assembly As shown in FIG. 2, one form of a safely shielded winged infusion assembly 21 comprises all the former and a sleeve-like trap 22 which slides over the body 13 to capture the wings and shield the needle 12 after sufficient retraction of the trailing tubing 16. It will be noted in this prior art form that projections 23 for finger placement are embodied on the trailing end of the sliding sleeve 22.

As shown in FIG. 3, another form of a safely shielded winged infusion assembly 31 comprises all the features shown in FIG. 1 and a needle trapping mechanism further comprising a flexible tether 32 attached to the trailing edge of the wings 14 and to a special form of hub 33 enclosing the trailing end of the needle 12. Needle capture and shielding is accomplished by traction on the special hub 33 or the trailing tubing 16 until the leading tip of the needle 12 is retracted behind a special spring-clip shown in FIGS. 10–12.

As shown in FIG. 4, a head-like projection or flange 41 can be added to the body 13 or to a sliding sleeve for purposes outlined below.

As shown in FIG. 5, the head-like projection 41 can further comprise antennae-like projections 51 with leading tabs 52 for increasing the area of surface contact, when a finger tip holds a pledget down over a venipuncture site to control venous bleeding, as well as to anchor the leading end of the winged infusion assembly 21 during needle withdrawal.

As shown in FIG. 6, the head-like projection 41, antenna-like projection 51, and leading tabs 52 can be small when applied to the body 13 of an alternate form of the shielded winged infusion assembly 31 shown in FIG. 3.

As shown in FIG. 7, the head-like projection 41 can be added in ovoid 71 or flange-like form during molding of the body 13 of the safely shielded winged infusion assembly 31.

As shown in FIG. 8, instead of a head-like projection, a leading means for anchoring the leading end of the winged infusion assembly 31 may comprise a loop attached to the leading edge of each wing 14.

As shown at a 90 degree angle and magnified ×2 in width in FIG. 9, the head-like projection 41, antennae-like projections 51 and leading tabs 52 extending from the leading end of a sleeve 22 sliding over the body 13 can be flat in profile, but angled dorsally such that these projections will not interfere with IV insertion of the needle in a given assembly. This view shows the paired slits 91 through which the butterfly wings are retracted to become entrapped in paired slots 92. It will be noted in this figure and in FIG. 5 that projections for finger placement are absent on the trailing end of the sliding sleeve 22.

As shown similarly in FIG. 10, in winged infusion assemblies 31 where the needle is trapped in the leading end of the body 13 by means of a ventral spring-clip 101, the head-like projection 41, antenna-like projections 52, and leading tabs 51 can be narrow and flat, but should be angled dorsally such that there is no interference with IV needle insertion.

As shown similarly in FIG. 11, in winged infusion assemblies 31 using ventral spring-clips 101 for capturing the needle, the head-like projection on the leading end of the body 13 can be ovoid 71 or flange-like 111 with an abrupt termination at the trailing end 112 for preventing slippage under finger pressure. The head can be molded from the same material as the body.

As shown similarly in FIG. 12, the head-like projections for anchoring can be substituted by a dorsally angled loop 81 emanating from the leading edge of each wing 14, and might be molded from wing material somewhat like the trailing tethers shown at 32 in FIG. 3.

In use, the anchoring means shown at 41, 51, 71, 81, 101 and 111 are designed such that the user of safer winged infusion assemblies shown at 21, 31 and in FIG. 5 can safely capture and shield the needle 12 after IV use in a patient without exposing the bevel or shank at any time. In addition, the anchoring means is designed such that the user can effectively control venous bleeding from the patient during and after needle withdrawal, using a finger tip of one hand placed over a pledget to anchor the winged infusion assembly and control venous bleeding simultaneously, while the other hand retracts the needle into a safe shield by means of trailing tubing 16 or a trailing needle hub 33. It should be added that such hand and pledget use have long been customary during the withdrawal of standard unshielded winged infusion assemblies.

It should be emphasized, further, that the dorsal head-like or flange-like projections shown in FIGS. 5–12 do not extend significantly beyond the leading end of the body 13 or the sleeve 22 which slides over the body 13, as opposed to the tethers claimed in U.S. Pat. Nos. 5,112,311 and 5,350,368 and, therefore, do not visually or structurally encumber accurate intravenous placement of the needle 12.

Finally, it should be appreciated by those skilled in the art of making and using winged infusion assemblies that the leading dorsal head projection means for finger control are exemplary, and subject to variation without departing from the spirit and scope of the invention.

Therefore, I claim:

1. A head-like projection for finger placement facing upward on the leading dorsal end of a puncture-resistant sleeve which slides over the body of a hollow needle to entrap and safely shield its sharp bevel and shank after use in a winged "butterfly" intravenous infusion assembly comprising the hollow needle with a trailing hub permanently attached to trailing tubing, in turn, attachable to an infusion source, and a body enclosed by concentric tubing to which paired wings for finger grasping are attached, said head-like projection comprising in a first preferred embodiment:

(a) an upward projecting head-like part located on the leading dorsal surface of a four-sided puncture-resistant plastic sleeve substantially longer than the total length of the hollow needle and having:

i. an essentially flat solid ventral surface;

ii. a closed leading end portion with a first aperture sized to transmit and initially leave exposed the sharp bevel and shank of the hollow needle without overlying sleeve parts other than an initially supplied disposable protective tube; a quadrangular body portion enclosing the body of the hollow needle along with the concentric tubing enclosing this body, and having lateral slots and slits on each side allowing the attached paired wings to protrude through; and a trailing end portion enabling mechanical closure of said four-sided puncture resistant sleeve leaving a second aperture sized to allow unrestricted passage of the trailing tubing therethrough;

iii. said quadrangular body portion having an elongated cavity of dimensions permitting the concentric tubing covering the body of the needle to slide through, and having on each lateral side leading slots and slits leading to trailing slots for guiding and trapping the paired wings attached to the concentric tubing enclosing the body of the hollow needle, such that traction on the hollow needle by means of the trailing tubing permanently attached to the hub of the hollow needle will cause said exposed sharp bevel and shank of the hollow needle to retract and become safely shielded within said elongated cavity in said body portion of said four-sided puncture-resistant plastic sleeve;

iv. said trailing end portion having no dorsal or lateral projecting parts modified for finger placement or grasping; and (b) whereon said upward projecting head-like part located dorsally on said leading portion of said four-sided puncture-resistant plastic sleeve slidingly attached over a winged intravenous infusion assembly does not encumber insertion of the sharp bevel and shank of the hollow needle into the vein of a patient when the paired wings are grasped together upright; but provides means in said elongated cavity for safely shielding the sharp bevel and shank of the hollow needle upon venous withdrawal when the user places a finger of one hand to exert enough downward pressure on said head-like projection to simultaneously occlude the underlying vein at the hollow needle insertion site and anchor said closed leading end portion of said four-sided puncture-resistant plastic sleeve, such that venous bleeding will be satisfactorily prevented and the sharp bevel and shank of the hollow needle will not be exposed during or after exerting sufficient traction on the trailing tubing with the opposite hand to safely entrap the paired wings into said trailing slots in said quadrangular body portion of said four-sided puncture-resistant plastic sleeve.

2. A head-like projection for finger placement, as in claim 1, alternatively comprising:

(a) said upward projecting head-like part located on the leading dorsal aspect of a tubular puncture-resistant sleeve having a leading end portion which initially leaves the sharp bevel and shank of the hollow needle entirely exposed without overlying sleeve parts other than said initially supplied disposable protective tube, a tubular body portion which slidingly encloses the body of the needle and to which the paired wings are attached laterally on each side, and a trailing end portion which limits trailing displacement of the hollow needle sliding through said tubular body portion by means of paired tethers attached to the trailing edge of each wing on one end and both attached to the trailing hub of the needle permanently attached to the trailing tubing on the other end, such that the sharp bevel and shank of the hollow needle can be slidingly and safely enclosed within said tubular body portion when a spring clip on the leading end of said tubular body portion closes the leading bore to prevent forward excursion of the hollow needle after sufficient retraction of the trailing hub on the hollow needle by means of the trailing tubing; and (b) whereon said head-like projection located dorsally on said leading portion of said tubular puncture-resistant sleeve does not encumber insertion of the sharp bevel and shank of the hollow needle into the vein of a patient when the paired wings are grasped together upright; but provides a means for safely shielding the sharp bevel and shank of the hollow needle upon venous withdrawal when the user places a finger of one hand to exert enough downward pressure on said head-like projection to simultaneously occlude the underlying vein at the hollow needle insertion site and anchor said leading end portion of said tubular puncture-resistant sleeve, such that venous bleeding will be satisfactorily prevented and the sharp bevel and shank of the hollow needle will not be exposed during or after exerting sufficient traction on the trailing tubing with the opposite hand to safely entrap the sharp bevel and shank within said leading bore of said tubular puncture-resistant sleeve.

3. a head-like projection for finger placement, as in claim 2 wherein said upward projecting head-like part is located as close as possible to leading end of said leading portion of the puncture-resistant sleeve, but does not extend beyond said first aperture; and is ovoid superiorly, but cut off in a trailing direction to present a sharply slanted edge to enhance finger anchoring, such that said downward pressure of said finger over said underlying vein and said anchorage of said puncture-resistant sleeve will both be optimized when a conventional sterile pledget is placed over the head-like projection for finger placement and said hollow needle intravenous insertion site before and during withdrawal of the sharp bevel and shank of the hollow needle from a selected vein.

4. A head-like projection for finger placement, as in claim 1 wherein said upward projecting head-like part is alternatively molded like the head of a butterfly having paired flexible antennae projecting forward and upward, but having tiny distal tabs on said paired antennae for enhancing finger-over-pledget anchorage of the leading doral end of the puncture resistant sleeve during and after said venous withdrawal of the sharp bevel and shank of the hollow needle.

5. A head-like projection for finger placement functionally as in claim 1 wherein said upward projecting head-like part on said leading end portion of the puncture-resistant sleeve is absent; and is substituted by an upward and forward projecting flexible tether which forms a loop permanently attached basally to the leading medial edge of each wing, said upward and forward projecting flexible tether being made sufficiently thin to not visually or substantially interfere with intravenous insertion of said exposed sharp bevel and shank of the hollow needle in a winged intravenous infusion assembly, but being useful for finger placement on said leading end portion of the puncture-resistant sleeve, such that satisfactory control of venous bleeding and shielding of the sharp bevel and shank of the hollow needle without exposure can be accomplished simultaneously as described.

6. A head-like projection for finger placement, as in claim 1 wherein said upward projecting head-like part is applicable to alternative forms of a puncture-resistant sleeve which slides over the body of a hollow needle to entrap and safely shield its sharp bevel and shank after use in a winged "butterfly" intravenous infusion assembly.

* * * * *